United States Patent [19]
Takahashi et al.

[11] Patent Number: 5,520,789
[45] Date of Patent: May 28, 1996

[54] GAS SENSOR USING IONIC CONDUCTOR

[75] Inventors: Hideaki Takahashi, Nisshin; Tadashi Inaba, Aichi-ken; Haruyoshi Kondo, Anjo, all of Japan

[73] Assignee: Kabushiki Kaisha Toyota Chuo Kenkyusho, Aichi-ken, Japan

[21] Appl. No.: 364,749

[22] Filed: Dec. 27, 1994

[30] Foreign Application Priority Data

Dec. 27, 1993 [JP] Japan .................................. 5-354122

[51] Int. Cl.$^6$ ................................................ G01N 27/409
[52] U.S. Cl. ........................................... 204/424; 204/426
[58] Field of Search ...................... 204/153.18, 421–429; 429/30, 33

[56] References Cited

U.S. PATENT DOCUMENTS

| | | | |
|---|---|---|---|
| 3,843,400 | 10/1974 | Radford et al. | 204/421 |
| 4,024,036 | 5/1977 | Nakamura et al. | 429/33 |
| 4,207,159 | 6/1980 | Kimura et al. | 204/425 |
| 4,257,863 | 3/1981 | Hoffman | 204/429 |
| 4,345,985 | 8/1982 | Tohda et al. | 204/425 |
| 4,668,375 | 5/1987 | Kato et al. | 204/425 |
| 4,940,528 | 7/1990 | Oki et al. | 204/426 |
| 5,288,388 | 2/1994 | Fombon | 204/416 |
| 5,344,547 | 9/1994 | Vlasov et al. | 204/435 |

*Primary Examiner*—T. Tung
*Attorney, Agent, or Firm*—Oblon, Spivak, McClelland, Maier & Neustadt

[57] ABSTRACT

A gas sensor using an ionic conductor has a thin-film gas detection portion on an alumina substrate. The gas detection portion comprises a zirconia ionic conductor layer, a pair of platinum electrodes provided with the ionic conductor layer interposed therebetween, and a pair of junction layers positioned between the ionic conductor layer and each electrode and formed in a state in which the substances of the ionic conductor layers and the electrodes are mixed therein.

The gas sensor using an ionic conductor is formed by sequentially forming a first electrode, a first junction layer, an ionic conductor layer, a second junction layer, and a second electrode by a physical vapor deposition method on a substrate, wherein the first and second junction layers are formed to be in a state in which the substances of the ionic conductor layers and the electrodes are both present.

12 Claims, 11 Drawing Sheets

GAS SENSOR USING IONIC CONDUCTOR

BACKGROUND OF THE INVENTION

1. Technical Field

The present invention relates to a gas sensor that uses an ionic conductor having a characteristic electrode configuration, and a method of fabricating the same.

2. Background Art

Solid ionic conductors can be divided into two main types: oxygen ionic conductors and proton conductors. Oxygen ionic conductors are currently coming into practical use and are used in fields such as oxygen sensors and oxygen separation technology.

On the other hand, it was discovered in 1979 that a sintered body of an oxide in which $SrCeO_3$ acts as a matrix exhibits a high level of proton conductance in an atmosphere containing hydrogen of water vapor (refer to preliminary paper 127 of the 20th Battery Forum (Nagoya), by Hiroyasu Iwahara, et al., which prompted research in the proton conductor field. However, the development of proton conductors has not yet reached a level at which they can be used in hydrogen sensors or in a hydrogen separation technology.

It is known to use a zirconia oxygen ionic conductor as an oxygen sensor. In such an oxygen sensor, platinum or a material in which platinum is the main component, such as Pt-Rh or Pt-Pd, is generally used as the electrode material. A platinum electrode is highly capable of converting oxygen gas into oxygen ions at its boundary with the zirconia oxygen ionic conductor, and moreover it is heat-resistant and extremely stable with respect to changes in the temperature of the atmosphere being measured. This platinum electrode is usually formed on the zirconia oxygen ionic conductor by a method such as chemical plating, printing, or physical vapor deposition (electron beam deposition or sputtering).

The resistance of a zirconia oxygen sensor is thought to be mainly the sum of the resistances of the zirconia ionic conductor itself and the electrode boundaries. Therefore, in order to reduce the resistance of the entire sensor, it is important to plan to reduce both the resistance of the zirconia ionic conductor itself and that of the electrode boundaries.

The boundary resistance is particularly difficult to control because it is affected by various factors such as the substance of each layer and the junction state, and the effective decrease the boundary resistance is expected. This boundary resistance is thought to be largely dependent on the state of the junction between the ionic conductor and the electrode.

One prior art method of reducing the boundary resistance between a zirconia ionic conductor layer and a platinum electrode is to increase the surface area of the zirconia ionic conductor layer, and thus increase the strength of the junction between the zirconia ionic conductor and the platinum electrode, by etching the surface with a strong alkaline liquid. However, this method does not provide sufficient adhesion between the two layers.

SUMMARY OF THE INVENTION

An objective of the present invention is thus to provide a gas sensor using an ionic conductor which enables an improvement in low-temperature operability and increases the density range of the gases to be measured, reducing the resistance of the boundary between the ionic conductor layer and each electrode, and which also has good reliability, stability, and thermal resistance. This invention also provides a method of fabricating this gas sensor using an ionic conductor.

The gas sensor of the present invention comprises:

an ionic conductor layer made of a first material;

a pair of electrodes made of a second material, disposed on the ionic conductor so that the ionic conductor layer is interposed between said pair of electrodes; and a pair of junction layers comprising a mixture of the first material and the second material, each one of the pair of junction layers being disposed between the ionic conductor layer and one of the pair of electrodes.

The junction layers of this gas sensor are preferably in a porous state.

The junction layers could be of a mixture of the materials of the electrodes and the ionic conductor, but it is preferable that the material of the ionic conductor is present in each junction layer to a ratio of at least 50 mol % overall, from considerations such as mechanical strength during thermal processing. It is also preferable that the composition ratios of the electrode material and the ionic conductor material vary continuously with depth of each junction layer. More specifically, the electrode material should be at a high ratio (such as 50 to 100 mol %) in each junction layer close to the boundary with the corresponding electrode, it should decrease gradually towards the boundary with the ionic conductor layer, and should be at a low ratio (such as 50 to 0 mol %) close to the boundary with the ionic conductor layer. Conversely, the ionic conductor material should be at a low ratio in each junction layer close to the boundary with the corresponding electrode, it should increase gradually towards the boundary with the ionic conductor layer, and should be at a high ratio close the boundary with the ionic conductor layer.

For an oxygen sensor, for example, the solid-state ionic conductor that forms the ionic conductor layer could be zirconia ($ZrO_2$), ceria ($CeO_2$), or thoria ($ThO_2$), and the zirconia could contain $Y_2O_3$, $Yb_2O_3$, or CaO to a density of 1 to 30 mol %.

For a hydrogen sensor, the ionic conductor layer could be a perovskite type of oxide formed of a solid solution of at least one element selected from In, Sc, Yb, Mg, Bi, Al, Ga, Y, or Nb, in a matrix of $CaZrO_3$.

The thickness of the junction layers would depend on the size of the gas sensor, but should normally be within the range of 10 to 10,000 Angstrom.

The method of fabricating the gas sensor of the present invention comprises the steps of forming a first electrode, a first junction layer, an ionic conductor layer, a second junction layer, and a second electrode in sequence by a physical vapor deposition method in a substrate, wherein the first and second junction layers are formed in a state in which the materials of the electrodes and ionic conductor layer are both present therein.

The physical vapor deposition method could be ion beam deposition, sputtering, or electron beam deposition. The use of any of these deposition methods enables accurate and simple control over factors such as film thickness and the composition ratio of the electrode and ionic conductor materials. The junction layers could be formed by a physical vapor deposition method such as ion beam deposition, multiple-source sputtering, or multiple-source electron beam deposition.

The advantages of using a physical vapor deposition method and the composition of ionic conductor layers formed by using such a physical vapor deposition method will now be described.

Figure 1:
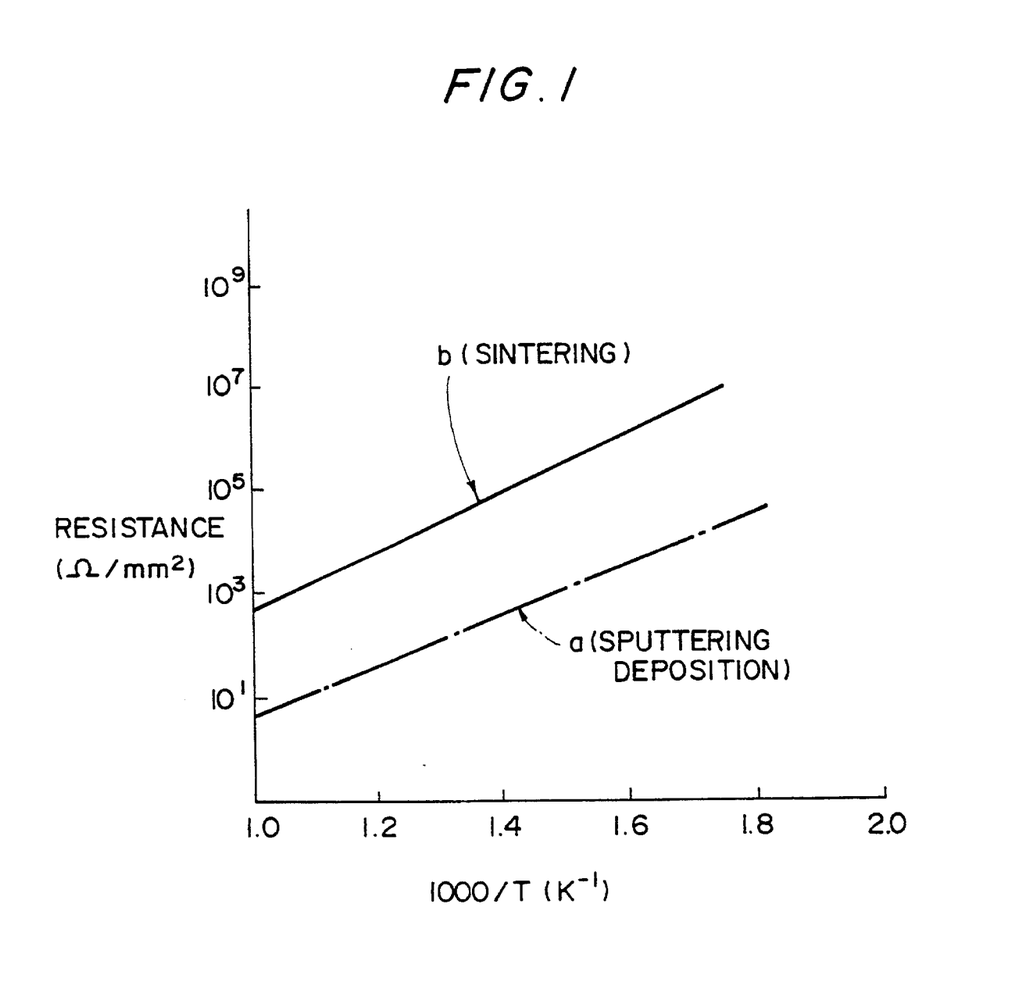
FIG. 1 is a graph showing the resistance-temperature characteristics of zirconia ionic conductor layers.

Ionic conductor layers were formed by using a sintering method and a sputtering method, as common methods of forming zirconia ionic conductor layers, and the results of investigating the resistances of these two types of ionic conductor layer are shown in FIG. 1. The line a in FIG. 1 is the resistance-temperature characteristic of an ionic conductor layer formed by sputtering and the line b is the resistance-temperature characteristic of an ionic conductor layer formed by sintering.

FIG. 1 demonstrates that, since the thickness of the ionic conductor layer formed by sputtering can be reduced to $\frac{1}{100}$ less than that of the ionic conductor layer formed by sintering, even though both ionic conductor layers used the same zirconia, a drop in resistance of approximately two orders of magnitude is possible.

Figure 2A:
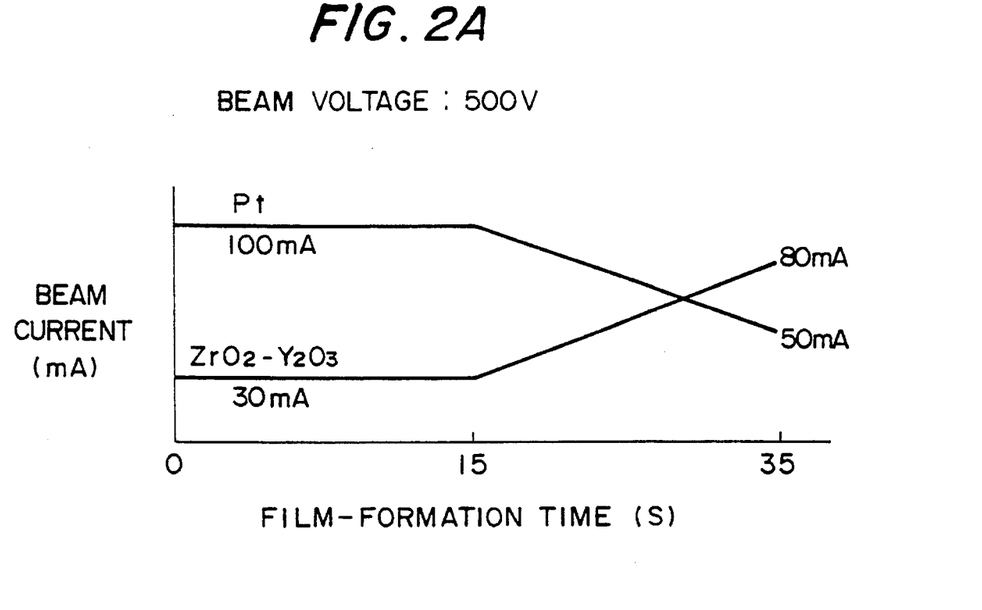
FIG. 2A is a graph of film-formation conditions for a stack of layers formed by using ion beam deposition.
Figure 2B:
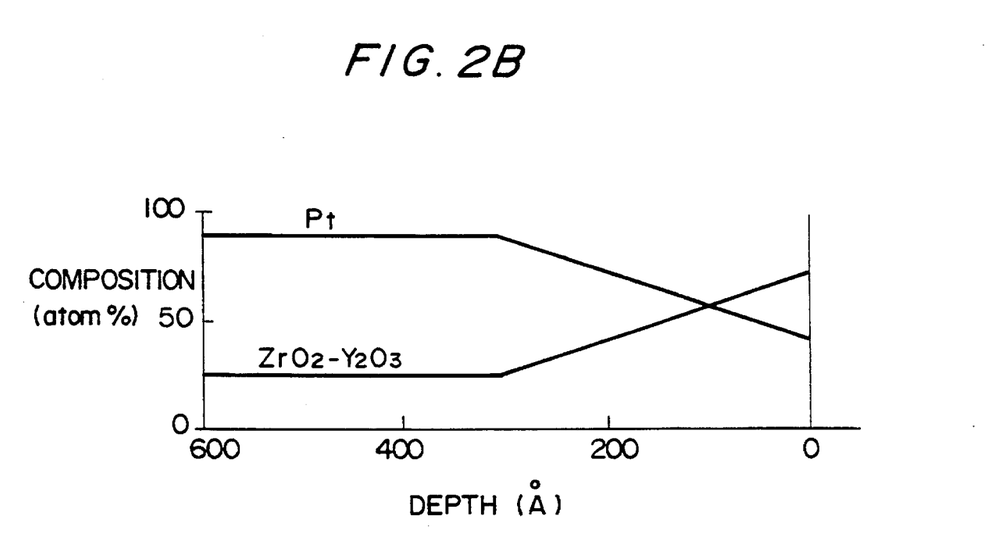
FIG. 2B is a graph of composition distribution in a stack of layers formed by ion beam deposition.

Changes in composition of a stack of layers formed by ion beam deposition, which is one physical vapor deposition method, are shown in FIG. 2. In these experiments, platinum and a mixed body of $ZrO_2$ and 8 mol % of $Y_2O_3$ were used as targets, a constant voltage was applied to the ion gun in an atmosphere of a degree of vacuum of $1\times10^{-4}$ Torr, and argon ions bombarded each target while the ion beam current output from the ion gun was controlled as shown in FIG. 2A, to form a stack of layers on an alumina substrate. Changes in the density of platinum and $ZrO_2$—$Y_2O_3$ with depth in the stacks of layer formed by this process were investigated by Rutherford backscattering spectrometry (RBS). The results are shown in FIG. 2B.

As can clearly be seen from FIG. 2B, it has been demonstrated that it is possible to form a multi-component layer stack in which the composition ratio corresponds fairly accurately to beam current, by controlling the beam current of argon ions bombarding the targets.

In the gas sensor using the ionic conductor of the present invention, the provision of junction layers between the ionic conductor layer and each electrode in which the materials forming the ionic conductor and electrode are mixed enables an increase in junction strength between the ionic conductor layer and the electrode and also a decrease in resistance at the boundary with the electrode. Mismatches in characteristics caused by physical differences between the ionic conductor and the electrode, such as their thermal conductivities, can also be suppressed. A gas sensor with the above junction configuration enables stable measurements, even with rapid operation, and also has superior thermal resistance and durability.

The fabrication method of the present invention enables the construction of a small gas sensor using an ionic conductor, in which the thickness and composition of layers formed by a physical vapor deposition method can be accurately controlled.

BRIEF DESCRIPTION OF THE DRAWINGS

FIG. 3A to FIG. 3F illustrates steps in the process of fabricating an oxygen sensor according to a first embodiment of the present invention;

FIG. 8A to FIG. 8E illustrates steps in the process of fabricating a proton sensor according to a third embodiment;

PREFERRED EMBODIMENTS OF THE INVENTION

The preferred embodiments of the present invention will be described below, with reference to drawings thereof.

FIRST EMBODIMENT

The first embodiment demonstrates how the present invention is applied to an oxygen sensor. An oxygen sensor 100 is configured of a first electrode (cathode) 14 of platinum, a first junction layer 20 of platinum and zirconia, a zirconia ionic conductor layer 16 that forms an electrolytic layer, a second junction layer 22 of platinum and zirconia, and a second electrode (anode) 18, formed in that sequence on one side of an alumina substrate 10, and a heater layer 12 formed of platinum on the other surface of the alumina substrate 10, as shown in FIG. 3F. In the oxygen sensor 100 of this configuration, the junction layers 20 and 22 of platinum and zirconia are formed between the zirconia ionic conductor layer 16 and the corresponding platinum electrodes 14 and 18. The composition ratio of platinum and zirconia in these junction layers 20 and 22 varies linearly with depth, as will be described later.

The process of fabricating this oxygen sensor 100 will now be described with reference to FIG. 3A to FIG. 3F.

Figure 3A:
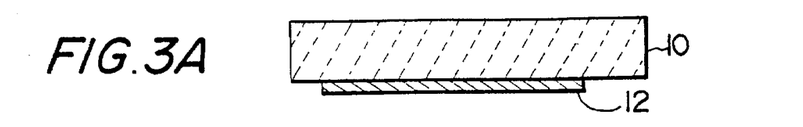

First, the heater layer 12 was formed of platinum on one surface of the alumina substrate 10 (FIG. 3A). This alumina substrate 10 was formed of porous alumina having a porosity of 10% with pores of 0.1 μm in diameter, and was approximately 0.3 mm thick. The heater layer 12 was formed by tightly attaching a stainless steel mask having a zigzag heater pattern slit onto the alumina substrate 10, and using an ion beam sputtering device (IBS device), sputtering device, or electron-beam deposition device to deposit an approximately 2 μm layer of platinum.

The first electrode 14, first junction layer 20, zirconia ionic conductor layer 16, second junction layer 22, and second electrode 18 that make up a gas detection portion were then formed in sequence and continuously by means such as an IBS device (FIG. 3B to FIG. 3F). The film-formation conditions during this process were as shown in FIG. 4. In the graph of FIG. 4, deposition time is plotted along the X-axis and the beam current of argon ions bombarding a platinum target or zirconia target is plotted along the Y-axis. The degree of vacuum of the IBS device was controlled to be 1×10$^{-4}$ Torr, the ion beam voltage was controlled to be 700 V, and the alumina substrate 10 and the substrate fixed portions attached to the alumina substrate 10 were controlled to be at room temperature.

Figure 3B:
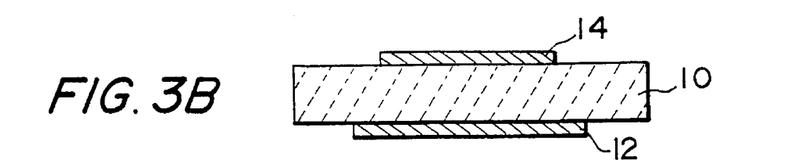
Figure 4:
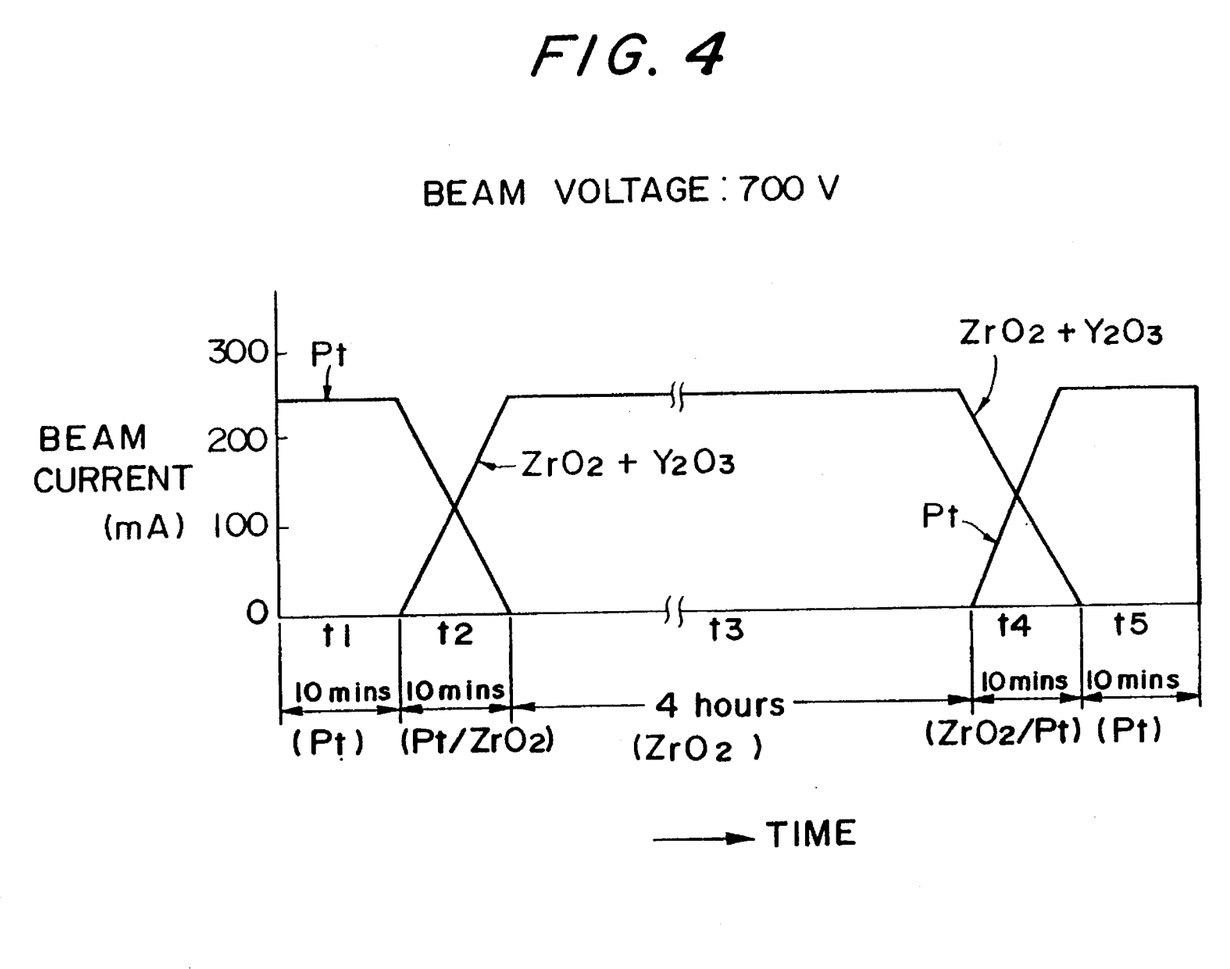
FIG. 4 is a graph showing film-formation conditions during the thin-film-formation process of FIG. 3.

More specifically, argon ions bombarded the platinum target at a beam current of approximately 250 mA for 10 minutes (t1) to deposit an approximately 1 μm layer of platinum to form the first electrode 14 (FIG. 3B).

Figure 3C:
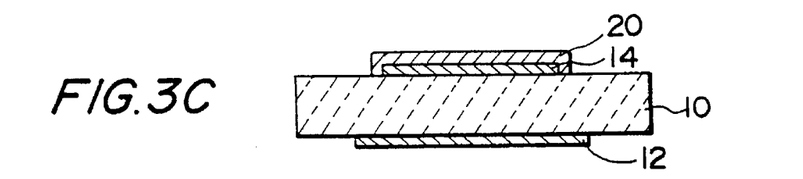

Next, the beam current for the platinum target was varied linearly from approximately 250 mA to 0 mA over 10 minutes (t2) and, at the same time, the beam current for the zirconia target was varied linearly from 0 mA to approximately 250 mA, to deposit the first junction layer 20 to a thickness of approximately 0.5 μm (FIG. 3C). The thus-formed first junction layer 20 was configured as a two-component layer in which the composition ratio of platinum and zirconia varied linearly in the direction from the boundary with the first electrode 14 toward the surface.

In other words, the amount of platinum in the first junction layer 20 was virtually 100% at the boundary with the first electrode 14, decreased linearly with depth toward the surface of the first junction layer 20, and was virtually 0% at the surface of the first junction layer 20. Conversely, the distribution of zirconia in the first junction layer 20 was opposite to that of platinum in that it was virtually 0% at the boundary with the first electrode 14, increased linearly with depth toward the surface of the first junction layer 20, and was virtually 100% at the surface of the first junction layer 20.

Figure 3D:
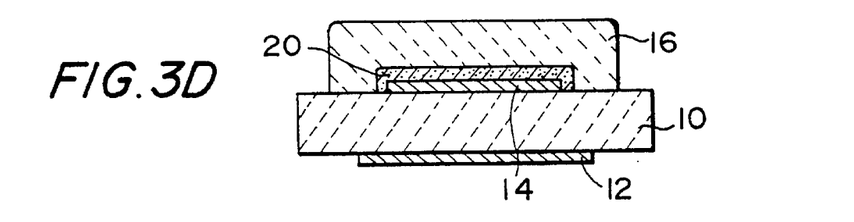

Argon ions then bombarded the zirconia target at a beam current of 250 mA for approximately 4 hours (t3), to form the zirconia ionic conductor layer 16 to a thickness of approximately 3 μm (FIG. 3D).

Figure 3E:
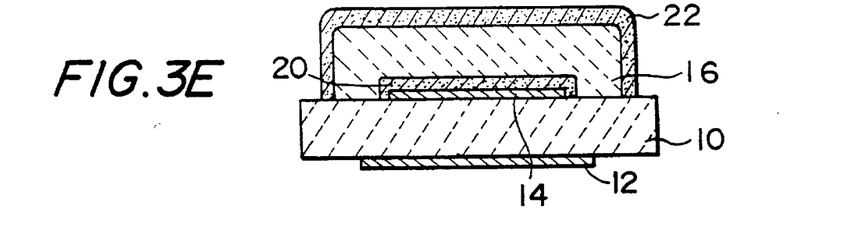
Figure 3F:
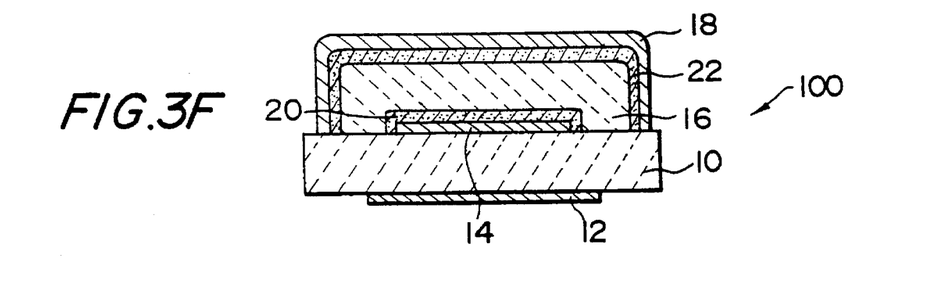

The second junction layer 22 was then formed to a thickness of approximately 0.5 μm by linearly varying the beam current for the zirconia target from approximately 250 mA to 0 mA over 10 minutes (t4) and, at the same time, linearly varying the beam current for the platinum target from 0 mA to approximately 250 mA (FIG. 3E). The composition ratio of the thus deposited layer was the opposite of that of the first junction layer 20 in that the density of zirconia decreased linearly from the boundary of the zirconia ionic conductor layer 16 toward the surface of the first junction layer 20, and that of platinum increased linearly.

The second electrode 18 was then formed by setting the beam current for the platinum target to approximately 250 mA for 10 minutes (t5) (FIG. 3F).

The above use of the IBS device enabled the continuous formation of the various layers that configure the detection portion of the oxygen sensor, and also enabled accurate setting of the thickness of each layer and the density distributions in the junction layers 20 and 22.

The complete oxygen sensor was configured by connecting platinum leads (not shown in the figures) to the first electrode (cathode) 14, second electrode (anode) 18, and heater layer 12 of the layered body (cell) formed in the above manner.

Sensor Characteristics

Figure 5:
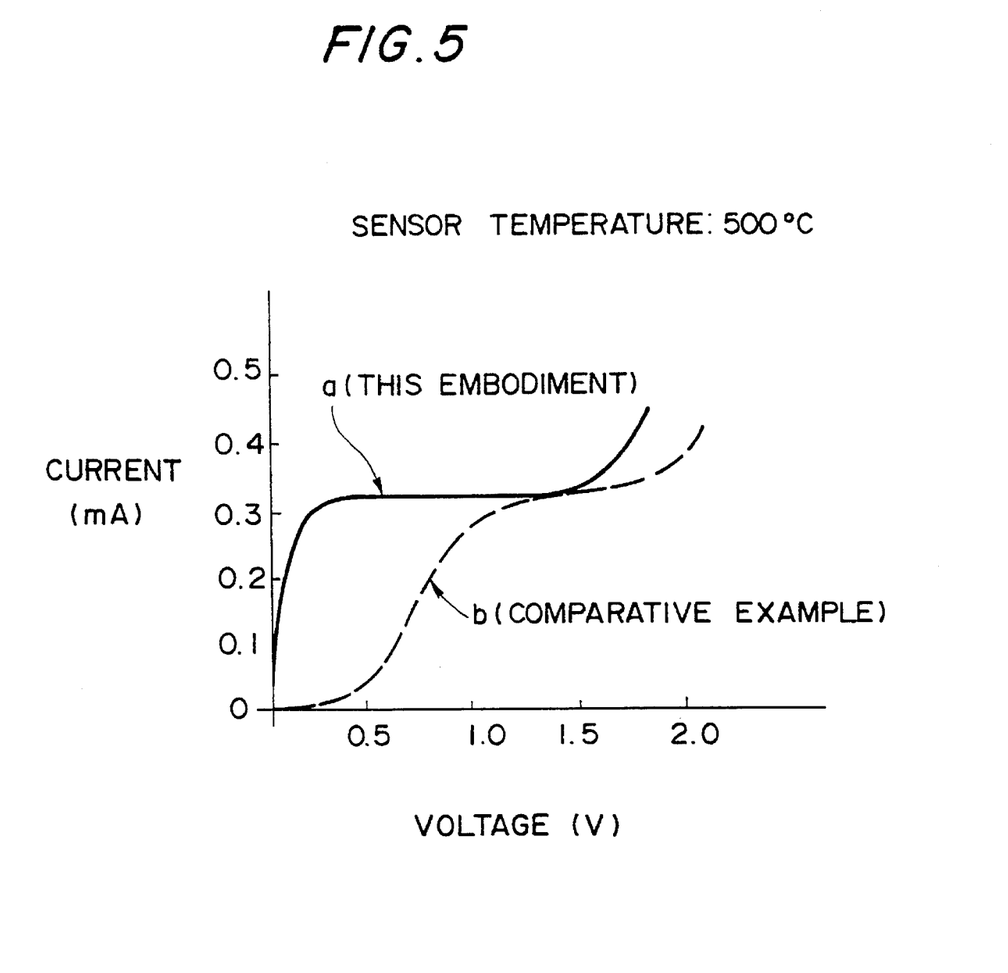
FIG. 5 is a graph showing the current-voltage characteristic of the oxygen sensor of the first embodiment, compared with that of a comparison oxygen sensor.

The current-voltage characteristics of the gas sensor obtained by the above described process were investigated. Measurements were done in the atmosphere and the heater temperature was set to 500° C. For comparison, the same current-voltage characteristics were obtained for a gas sensor having the same configuration as the gas sensor of the present embodiment, but without junction layers (comparative example). The results of these measurements are shown in FIG. 5. The curve a in FIG. 5 is the current-voltage characteristic of the gas sensor of this embodiment and the curve b is that of the comparative example.

The results shown in FIG. 5 demonstrate that the gas sensor of this embodiment provided a lower sensor resistance and a preferable limiting current characteristic, in comparison with the gas sensor of the comparative example.

Figure 6:
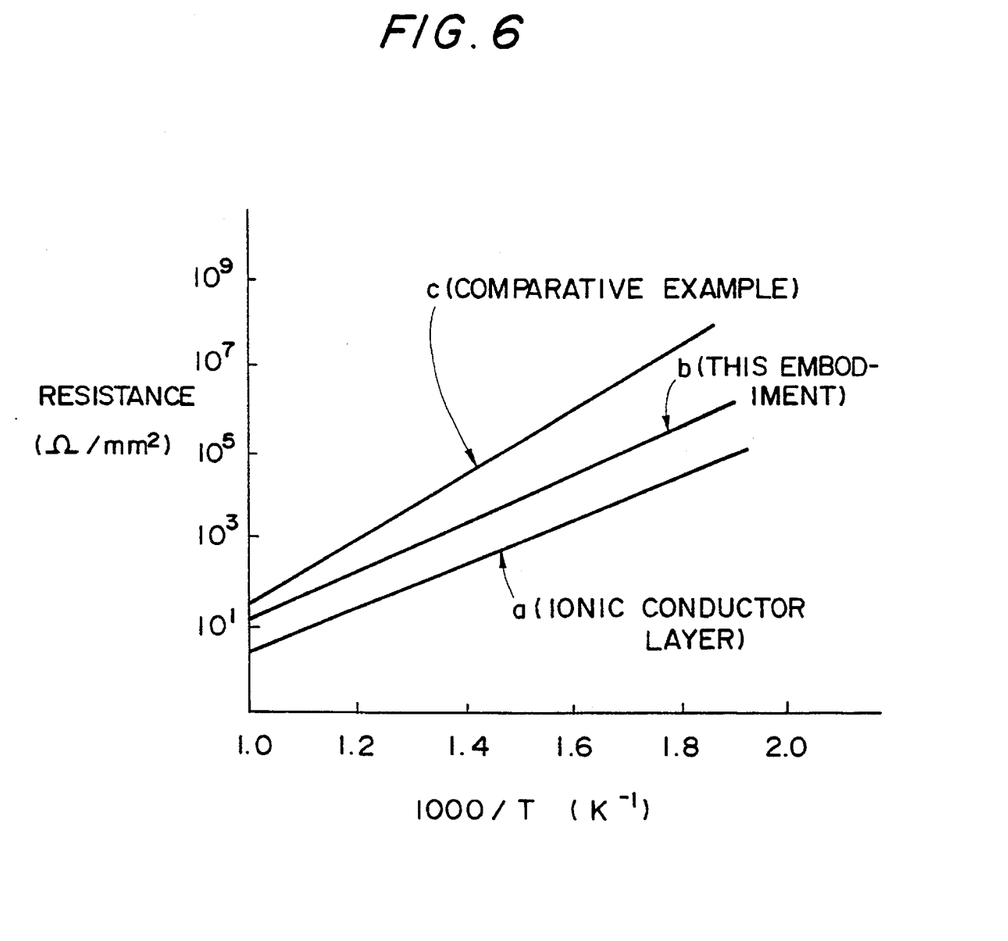
FIG. 6 is a graph of the resistance-temperature characteristics of the ionic conductor layer and electrode boundary in the gas sensor of the first embodiment, compared with those of a comparative example.

The resistance-temperature characteristics of the gas sensor of this embodiment and the comparative gas sensor were also investigated, using the complex-impedance law. The results of these measurements are shown in FIG. 6. The line a in FIG. 6 is the resistance-temperature characteristic of an ionic conductor layer by itself, the line b is that at the electrode boundaries of this embodiment, and the line c is that at the electrode boundaries of the comparative example.

As is clear from FIG. 6, the electrode boundary resistance of the gas sensor of the comparative example is close to two orders of magnitude greater than that of a zirconia ionic conductor layer by itself, while the boundary resistance of the gas sensor of this embodiment is about one order of magnitude greater than that of a zirconia ionic conductor layer by itself. Thus it has been demonstrated that the provision of junction layers in which the materials of the electrode and ionic conductor layers are mixed enables a dramatic reduction in the boundary resistance of the gas sensor.

SECOND EMBODIMENT

The gas sensor of this second embodiment has the same basic configuration as that of the oxygen sensor 100 of the first embodiment (FIG. 3F), except that the porous structures of the electrodes 14 and 18 and the junction layers 20 and 22 differ from those of the first embodiment. These changes in the porosities of the electrode and junction layers not only make it easier for oxygen to reach the electrode boundaries or the boundaries with the zirconia ionic conductor layer 16, but also greatly increase the surface areas of these boundaries. As a result, improvements can be expected in that the efficiency with which the oxygen is converted into oxygen ions at the electrode boundaries is increased, the sensitivity and responsiveness of the sensor are improved, and the hysteresis characteristic is reduced.

The above porous electrodes and junction layers are created as described below for the oxygen sensor 100 with the same process as that for fabricating the first embodiment shown in FIG. 3.

Figure 7:
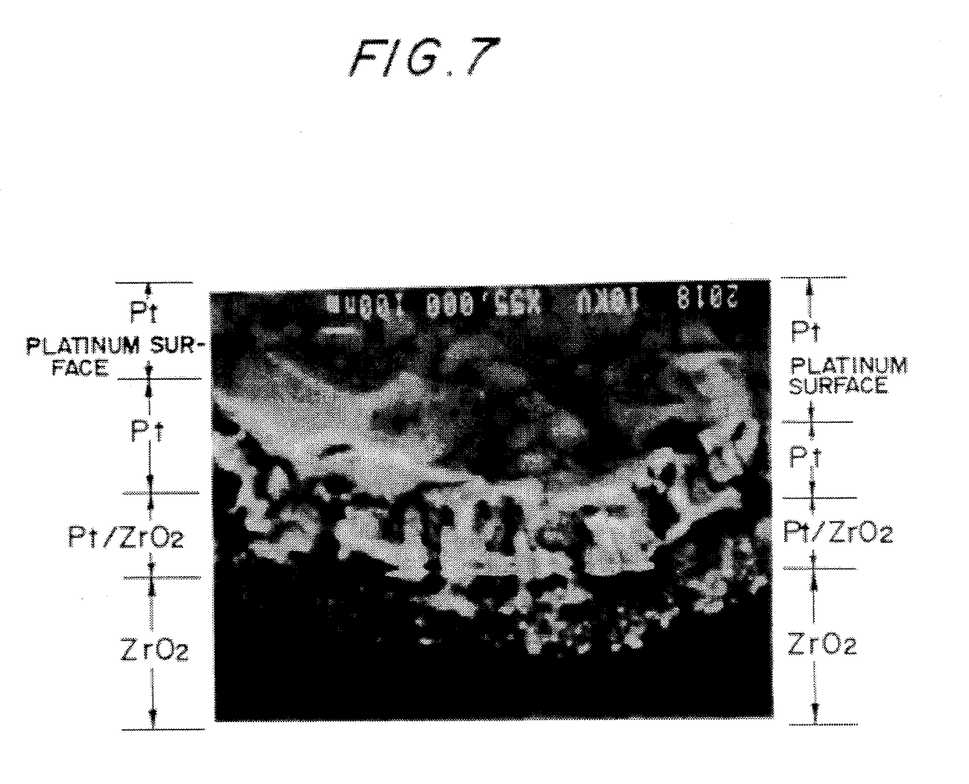
FIG. 7 is an electron micrograph of the granular structure of a detector portion of an oxygen sensor of a second embodiment.

First, a voltage is applied to the detector portion while the gas sensor is heated in the atmosphere to between 600° and 1000° C., such as 800° C., so that a current of approximately 0.01 to 1 mA/mm$^2$ flows therethrough, and the current continues to flow as the polarity of the electrodes is changed. This process of passing a current through the detector portion changes the platinum in the electrodes and junction layers into a granular state in accordance with the conversion of oxygen gas into oxygen ions. As a result, pinholes having a diameter of approximately 0.1 μm or less are generated within the electrodes and junction layers. An electron micrograph of a cross-section through the electrode and junction layer at a magnification of 55,000 times is shown in FIG. 7. FIG. 7 demonstrates that the electrode and junction layer had been formed in a porous state.

THIRD EMBODIMENT

This third embodiment concerns a proton sensor to which the present invention is applied. This proton sensor 200 comprises a first electrode 14 of platinum, a first junction layer 30 of platinum and a $CaZrO_3$—$In_2O_3$ perovskite type of oxide (hereinafter abbreviated simply to "$CaZrO_3$"), a proton conductor layer 36 of $CaZrO_3$, a second junction layer 32 of $CaZrO_3$ and platinum, and a second electrode 18 of platinum, formed in that sequence on one side of an alumina substrate 10, as shown in FIG. 8E. A heater layer 12 of platinum is formed on the other surface of the alumina substrate 10.

The process of fabricating this proton sensor 200 will now be described with reference to FIG. 8A to FIG. 8F.

Figure 8A:
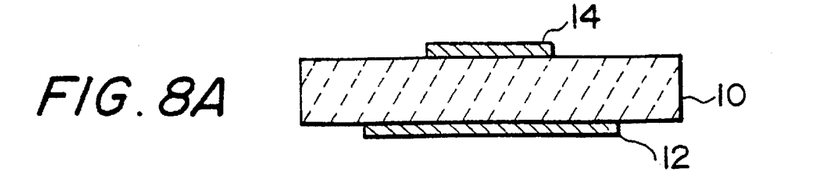

First, the heater layer 12 is formed of platinum on one surface of the alumina substrate 10 (FIG. 8A). This alumina substrate 10 had a porosity of 5% with pores of 0.01 μm in diameter, and was approximately 0.3 mm thick. The heater layer 12 was formed by tightly attaching a stainless steel mask having a zigzag heater pattern slit onto the alumina substrate 10, and having a sputtering device, IBS device, or electron-beam deposition device to deposit an approximately 2 μm layer of platinum.

The first electrode 14, the first junction layer 30, the proton conductor layer 36, the second junction layer 32, and the second electrode 18 which compose a gas detector portion were then formed in sequence and continuously by means such as an IBS device (FIG. 8B to FIG. 8F). The film-formation conditions during this process were as shown in FIG. 9.

Figure 9:
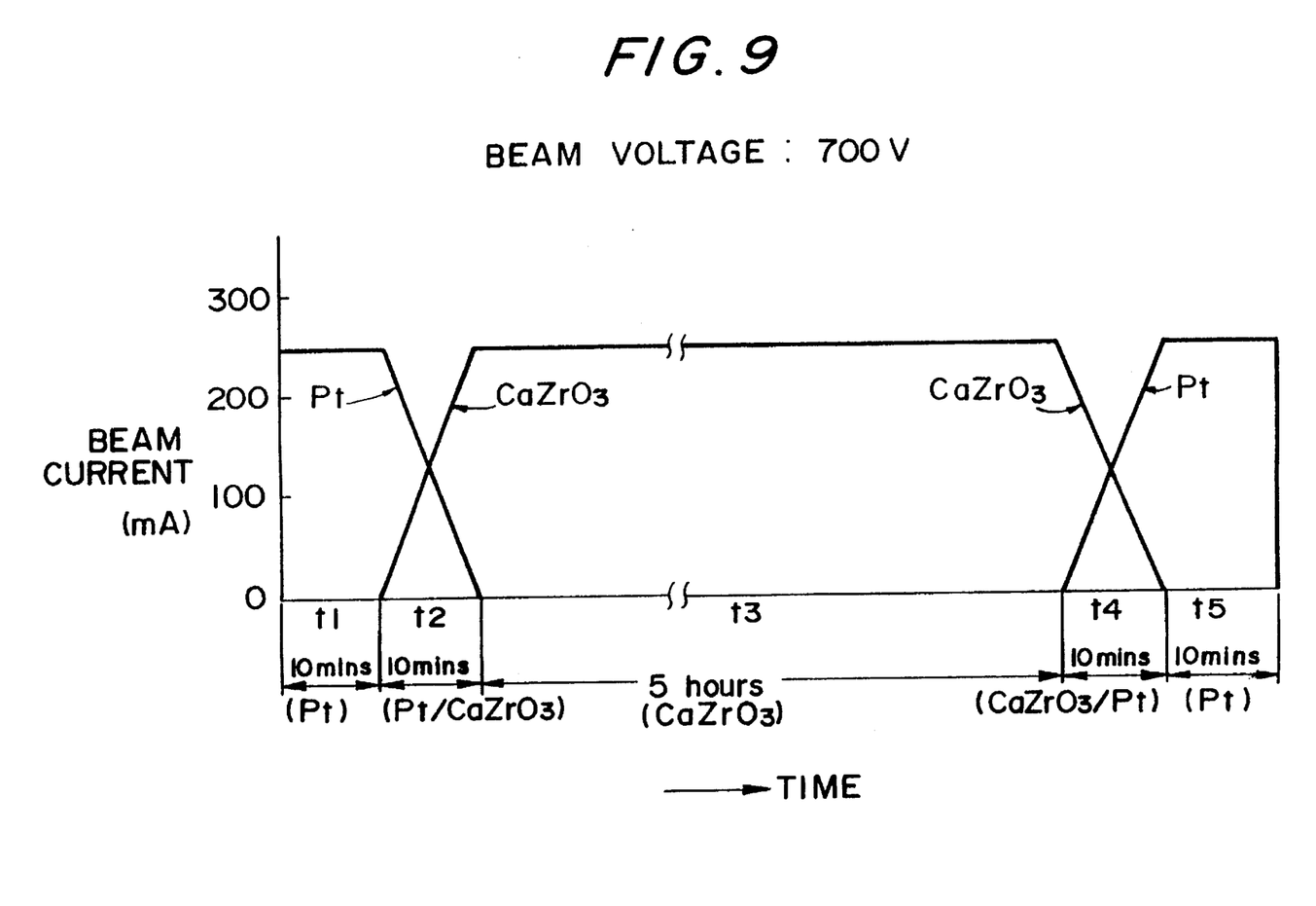
FIG. 9 is a graph showing film-formation conditions during the thin-film-formation process of FIG. 8.

In the graph of FIG. 9, deposition time is plotted along the X-axis and the beam current of argon ions bombarding a platinum target of $CaZrO_3$ target is plotted along the Y-axis. The degree of vacuum of the IBS device was $1 \times 10^{-4}$ Torr, the ion beam voltage was controlled to be 900 V, and the heating of the substrate fixed portions attached to the alumina substrate 10 was controlled to 300° C.

Figure 8B:
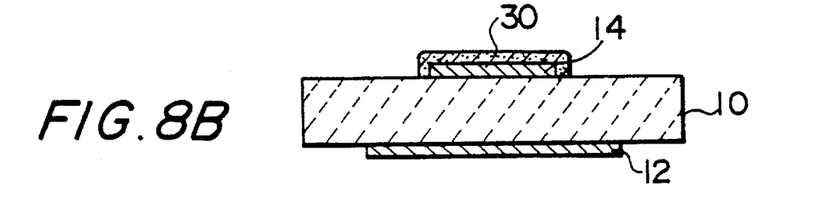

More specifically, argon ions bombarded the platinum target at a beam current of approximately 250 mA for approximately 10 minutes (t1) to deposit an approximately 1 μm layer of platinum to form the first electrode 14 (FIG. 8A). Next, the beam current for the platinum target was varied linearly from approximately 250 mA to 0 mA over 10 minutes (t2) and, at the same time, the beam current for the $CaZrO_3$ target was varied linearly from 0 mA to approximately 250 mA, to deposit the first junction layer 30 to a thickness of 0.3 μm (FIG. 8B). The thus-formed first junction layer 30 was formed as a two-component layer in which the composition ratio of platinum and $CaZrO_3$ varied linearly in the direction from the boundary with the first electrode 14 toward the surface.

In other words, the amount of platinum in the first junction layer 30 was virtually 100% at the boundary with the first electrode 14, decreased linearly with depth toward the surface of the first junction layer 30, and was virtually 0% at the surface of the first junction layer 30. Conversely, the distribution of $CaZrO_3$ in the first junction layer 30 was opposite to that of platinum in that it was virtually 0% at the boundary with the first electrode 14, increased linearly with depth toward the surface of the first junction layer 30, and was virtually 100% at the surface of the first junction layer 30.

Figure 8C:
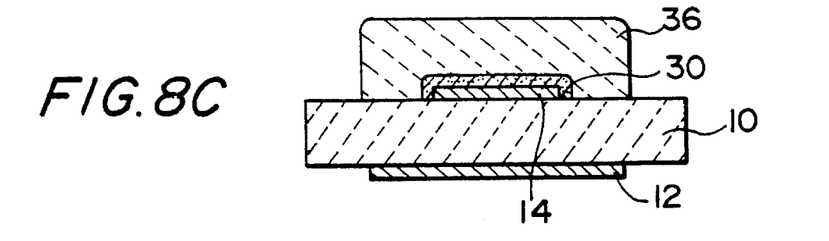
Figure 8D:
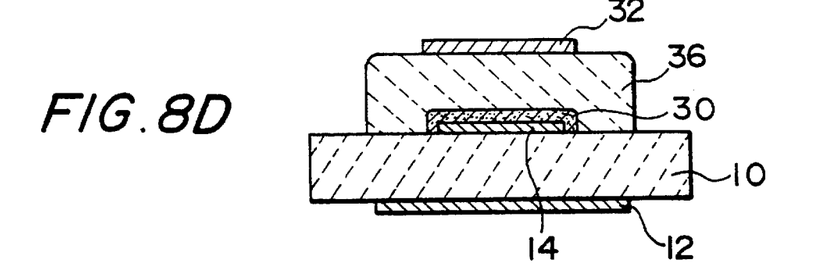
Figure 8E:
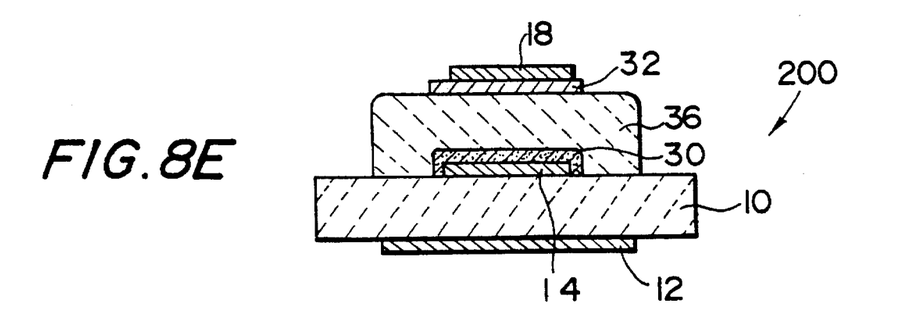

Argon ions then bombarded the $CaZrO_3$ target at a beam current of 250 mA for approximately 5 hours (t3), to form the $CaZrO_3$ proton conductor layer 36 to a thickness of approximately 5 μm (FIG. 8C). The second junction layer 32 was then formed to a thickness of approximately 0.3 μm by linearly varying the beam current for the $CaZrO_3$ target from approximately 250 mA to 0 mA over 10 minutes (t4) and, at the same time, linearly varying the beam current for the platinum target from 0 mA to approximately 250 mA (FIG. 8D).

The composition ratio of the thus deposited layer was the opposite of that of the first junction layer 30 in that the density of $CaZrO_3$ decreased linearly from the boundary of the $CaZrO_3$ proton conductor layer 36 toward the surface of the first junction layer 30, and that of platinum increased linearly.

The second electrode 18 was then formed by setting the beam current for the platinum target to approximately 250 mA for 10 minutes (t5) (FIG. 8E).

The above use of the IBS device enabled the continuous formation of the various layers that constitute the detection portion of the gas sensor, and also enabled accurate setting of the thickness of each layer and the density distributions in the junction layers 30 and 32.

The complete proton sensor 200 was configured by connecting platinum leads (not shown in the figures) to the first electrode (cathode) 14, second electrode (anode) 18, and heater layer 12 of the layered body formed in the above manner.

Sensor Characteristics

Figure 10:
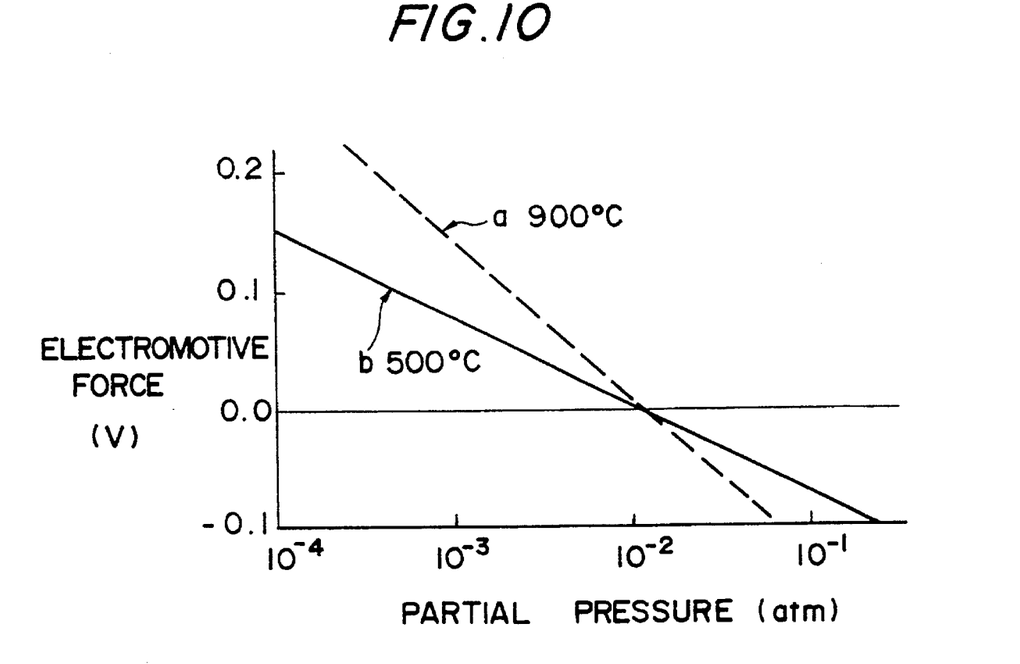
FIG. 10 is a graph showing electromotive-force—partial-pressure characteristics relating to the proton sensor of the third embodiment.

A hydrogen concentration cell was created by varying the concentration of hydrogen in a hydrogen gas atmosphere between the substrate side and detection portion side of the proton sensor 200 obtained by the above described process, and the electromotive force characteristics thereof were investigated. The results are shown in FIG. 10. In FIG. 10, the line a is the electromotive-force—partial-pressure characteristic obtained when the gas temperature was 900° C., and the line b is that when the gas temperature is 500° C. The results shown in FIG. 10 demonstrates that the proton sensor of this embodiment exhibits proton conductivity at high temperatures such as over 500° C.

Figure 11:
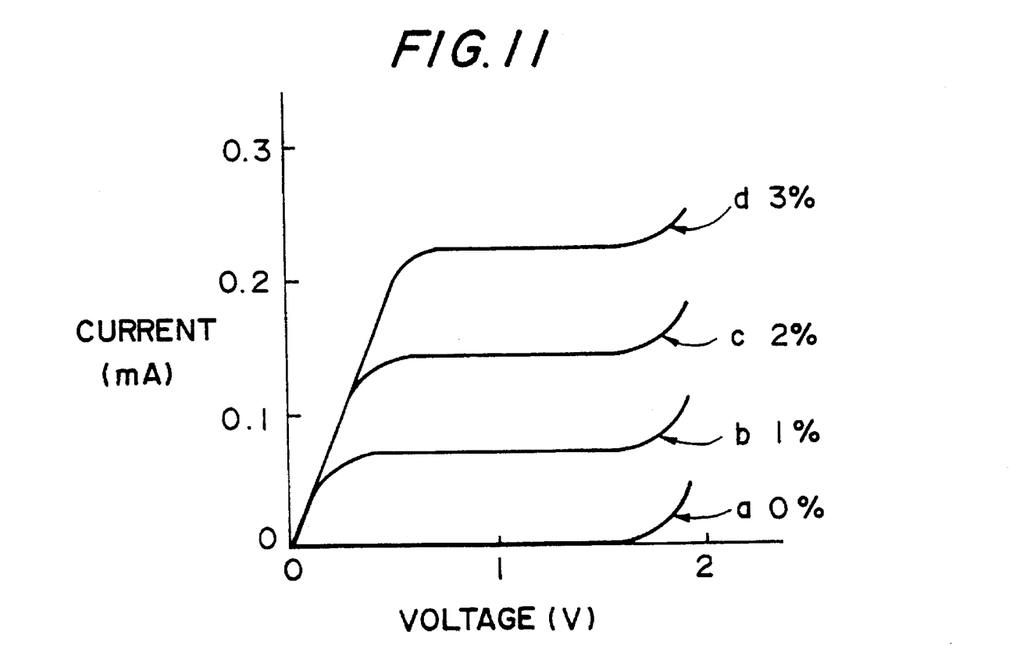
FIG. 11 is a graph of current-voltage characteristics relating to the proton sensor of the third embodiment.

The current-voltage characteristic of the proton sensor 200 of this embodiment were next investigated. In these experiments, the current-voltage characteristic was measured with the proton sensor 200 in a constant-temperature electrical furnace at 700° C., while the hydrogen density was varied in steps within the range of 0 to 3%. The results are shown in FIG. 11. The curve a in FIG. 11 is the current-voltage curve when the hydrogen density was 0%, the curve b is that when the hydrogen density was 1%, the curve c is that when the hydrogen density was 2%, and the curve d is that when the hydrogen density was 3%.

As can clearly be seen from FIG. 11, a limiting current corresponding to the hydrogen density is obtained by the proton sensor of this embodiment, and thus it is confirmed that it can accurately measure proton densities.

Figure 12:
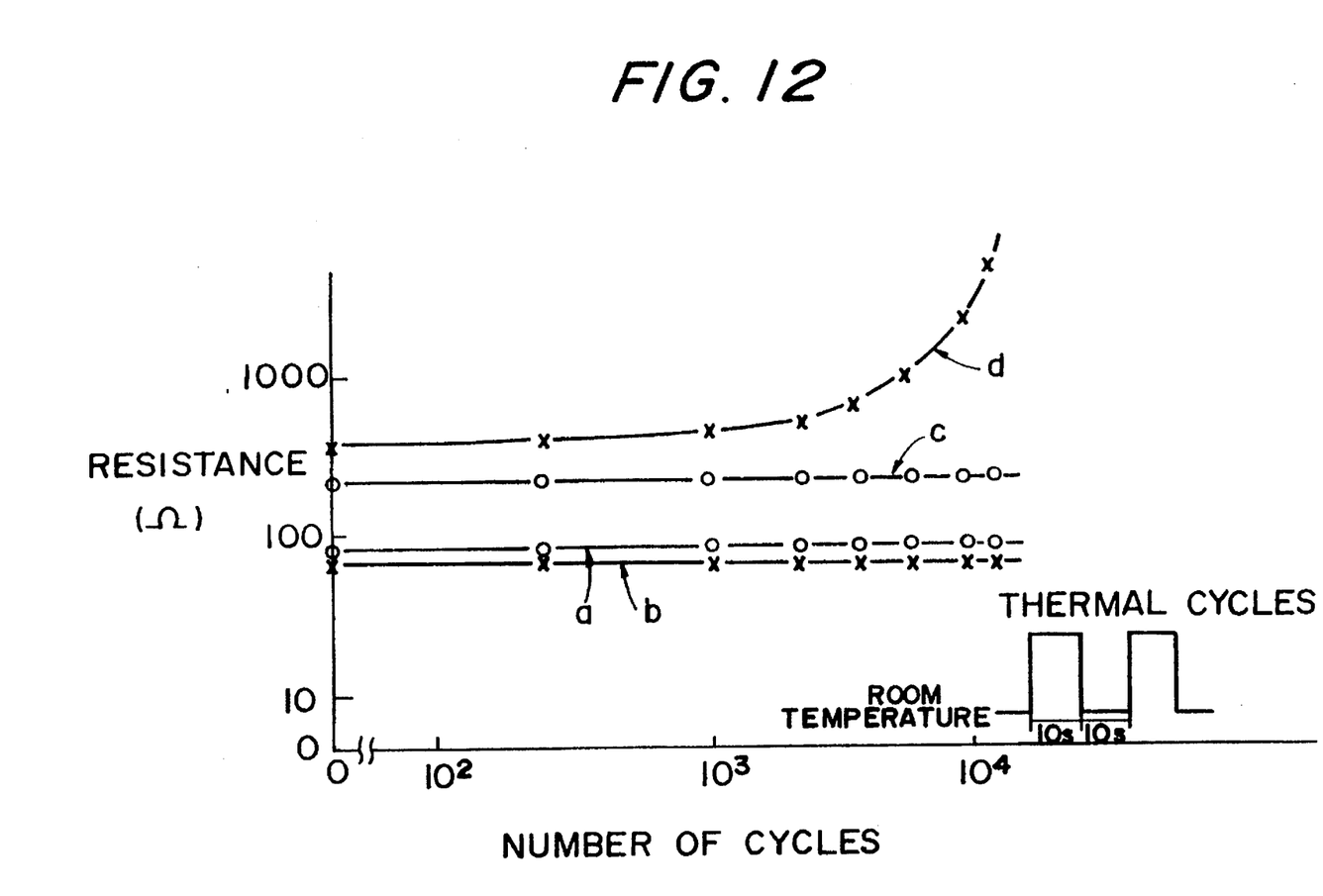
FIG. 12 is a graph of the resistance-heat cycle characteristics of the proton conductor layer and the electrode boundary of the proton sensor of the third embodiment, together with those of a comparative proton sensor.

Changes in resistance of the proton sensor 200 with thermal cycles were also investigated. A comparative proton sensor which had the same configuration as this embodiment, but without the first junction layer 30 and the second junction layer 32, was also tested, and changes in resistance with numbers of thermal cycles were investigated. These experiments were performed at room temperature (25° C.) in a nitrogen atmosphere containing 1% hydrogen and 1% water vapor, and the temperature of the proton sensor was varied by a heater in a cycle of increased temperature (700°

C.) and reduced temperature (25° C.) with a cycle of 20-second period that was repeated through 10,000 cycles. During this process, the resistances of the proton conductor layer 36 and the electrode boundaries were measured by complex-impedance methods. The results are shown in FIG. 12. The curve a in FIG. 12 is resistance—temperature-cycle characteristic for the ionic conductor layer alone of this embodiment, the curve b is that of the ionic conductor layer alone of the comparative example, the curve c is that of the electrode boundaries of this embodiment, and the curve d is that of the electrode boundaries of the comparative example.

As can clearly be seen from FIG. 12, these experiments showed that the resistances of the ionic conductor layers of both this embodiment and the comparative example varied hardly at all over the entire period from the start of the thermal cycles to the end. Similarly there was virtually no variation seen in the resistance of the electrode boundaries in the proton sensor of this embodiment over the entire period of the thermal cycles, demonstrating that this embodiment has extremely good stability with respect to thermal variation. In contrast, however, the resistance of the electrode boundaries in the comparative example gradually increased as the number of thermal cycles increased, demonstrating that good stability with respect to thermal cycles could not be obtained.

What is claimed is:

1. A gas sensor using an ionic conductor, comprising:
    an ionic conductor layer made of a first material;
    a pair of electrodes made of a second material, disposed on said ionic conductor so that said ionic conductor layer is interposed between said pair of electrodes; and
    a pair of junction layers comprising a mixture of said first material and said second material, each one of said pair of junction layers being disposed between said ionic conductor layer and one of said pair of electrodes;
    wherein the ratio of a content of said first material to a content of said second material with respect to a whole molecular amount of said mixture varies continuously along the depth of said pair of junction layers.

2. A gas sensor using an ionic conductor according to claim 1, wherein:
    said pair of junction layers are in a porous state.

3. A gas sensor using an ionic conductor according to claim 1, wherein:
    a content of said first material in said pair of junction layers is at least 50 mol % with respect to a whole molecular amount of said mixture.

4. A gas sensor using an ionic conductor according to claim 1, wherein:
    a content of said first material in said pair of junction layers is low near said pair of electrodes and high near said ionic conductor layer; and
    a content of said second material in said pair of junction layers is high near said pair of electrodes and low near said ionic conductor layer.

5. A gas sensor using an ionic conductor according to claim 1, wherein:
    said ratio varies linearly along the depth of said pair of junction layers.

6. A gas sensor using an ionic conductor according to claim 1, wherein:
    said ionic conductor layer is a conductor of oxygen ions.

7. A gas sensor using an ionic conductor according to claim 6, wherein:
    said ionic conductor layer comprises at least one element selected from the group consisting of zirconia, ceria, and thoria.

8. A gas sensor using an ionic conductor according to claim 7, wherein:
    said ionic conductor layer comprises zirconia and at least one element selected from the group consisting of $Y_2O_3$, $Yb_2O_3$, and CaO, the content of said element being 1 to 30 mol % with respect to a whole molecular amount of said ionic conductor layer.

9. A gas sensor using an ionic conductor according to claim 1, wherein:
    said ionic conductor layer is a conductor of hydrogen ions.

10. A gas sensor using an ionic conductor according to claim 9, wherein:
    said ionic conductor layer comprises a perovskite oxide in which at least one element is dissolved in a material of $CaZrO_3$, said at least one element being selected from the group consisting of indium, scandium, ytterbium, magnesium, bismuth, aluminum, gallium, yttrium, and niobium.

11. A gas sensor using an ionic conductor, comprising:
    a substrate having opposing surfaces;
    a first electrode formed of a first material on one surface of said substrate;
    a first junction layer formed of a mixture of said first material and a second material on said first electrode;
    an ionic conductor layer formed of said second material on said first junction layer;
    a second junction layer formed of a mixture of said first and second materials on said ionic conductor layer; and
    a second electrode formed of said first material on said second junction layer;
    wherein the ratio of a content of said first material to a content of said second material with respect to a whole molecular amount of said mixture varies continuously along the depth of said pair of junction layers.

12. A gas sensor using an ionic conductor according to claim 11, wherein:
    a heater layer is provided on the other surface of said substrate.

* * * * *